United States Patent [19]
Klesges

[11] Patent Number: 5,942,255
[45] Date of Patent: Aug. 24, 1999

[54] METHODS OF ENHANCING LEAN TISSUE MASS AND BONE MINERAL CONTENT AND COMPOSITIONS THEREFOR

[75] Inventor: Robert C. Klesges, Memphis, Tenn.

[73] Assignee: The University of Memphis, Memphis, Tenn.

[21] Appl. No.: 08/680,060

[22] Filed: Jul. 15, 1996

[51] Int. Cl.⁶ .......................... A61K 33/06; A61K 33/08; A61K 33/14; A61K 31/195
[52] U.S. Cl. .......................... 424/682; 424/678; 424/686; 424/687; 424/688; 424/693; 424/696; 424/697; 514/167; 514/168; 514/904; 514/905; 514/558; 514/560; 514/574
[58] Field of Search ...................................... 424/678, 682, 424/686, 687, 688, 693, 696, 697; 514/167, 168, 904, 905, 558, 560, 594; 426/73, 74, 599, 330.5

[56] References Cited

U.S. PATENT DOCUMENTS

| | | | |
|---|---|---|---|
| 4,994,449 | 2/1991 | Leonard | 514/171 |
| 5,232,709 | 8/1993 | Saltman et al. | 424/630 |
| 5,403,831 | 4/1995 | DeLuca et al. | 514/167 |

FOREIGN PATENT DOCUMENTS

| | | |
|---|---|---|
| 2381 543 A5 | 8/1990 | German Dem. Rep. . |
| 5-147653 | 12/1993 | Japan . |
| 2 192 131 | 1/1988 | United Kingdom . |
| 2 196 523 | 5/1988 | United Kingdom . |
| WO 92/19251 | 11/1992 | WIPO . |
| WO 93/12672 | 7/1993 | WIPO . |

OTHER PUBLICATIONS

Suominen H. *Bone mineral density and long term exercise: An overview of cross–sectional athlete studies.* Sports Med 1993; 16:316–330.

Marcus R, Carter DR. *The role of physical activity in bone mass regulation.* Adv Sports Med Fitness 1988; 1:63–82.

Bilanin J, Blanchard M, Russek–Cohen. E. *Lower vertebral bone density in male long distance runners.* Med Sci Sports Exer 1989; 21:66–70.

MacDougall JD, Webber CE, Martin J. Ormerod S, Chesley A Younglai EV, Gordon CL, Blimkie CJR. *Relationship among running mileage, bone density, and serum testosterone in male runners.* J. Applied Physiol 1992; 73:1165–1170.

Hetland ML, Haarbo J, Christiansen C. *Low bone mass and high bone turnover in male long distance runners.* J Clin Endocrinol Metab 1993; 77:770–775.

Rico H, Revilla M, Villa LF, Gómez–Castresana F. Del Buergo MA. *Body composition in potpuberal box cyclists.* J Sports Med Phys Fittness 1993; 33:278–281.

Williams MH. *Vitamin supplementation and athletic performances,* Int J Vitam Nutr Res Suppl 1989; 30:163–191.

Palmieri GMA. *Calcium: Why and how much?* Miner Electrolyte Metab 1995; 21:236–241.

Matkovic V, Fontana D, Tominac C, Goel P, Chesnut CH. *Factors that influence peak bone mass formation: A study of calcium balance and the inheritance of bone mass in adolescent females.* Am J Clin Nutr 1990; 52:878–888.

Rourke, Kathleen Marie, "The Effect of Calcium Supplementation on Bone Mineral Dnesity in Female Athletes Engaged in Weight–Bearing VS. Non–Weight Bearing Activities" Syracuse University (1994).

Beltz, Susan Durden et al., "Efficacy of Nutritional Supplements Used by Athletes," Clinical Pharmacy, vol. 12, Dec. 1993, pp. 900–908.

Dissertation Abstracts, Dissabs 95:6615 (1994).

Patent Abstracts of Japan Publication JP 05336924 Dec. 21,1993 Masanori et al.

*Primary Examiner*—John Pak
*Attorney, Agent, or Firm*—Needle & Rosenberg, PC

[57] ABSTRACT

The invention is directed to a method of enhancing lean tissue mass in a subject by administering calcium to the subject, thereby enhancing the lean tissue mass in the subject. The invention is also directed to a method of enhancing bone mineral content in a physically active subject comprising administering calcium to the subject, thereby enhancing the bone mineral content in the subject. The invention is also directed to a method of enhancing bone mineral content and of enhancing lean tissue mass in a subject comprising administering calcium to the subject, thereby enhancing the bone mineral content and enhancing the lean tissue mass in the subject. The invention is further directed to a milk-free composition for enhancing bone mineral content and/or for enhancing lean tissue mass in a physically active subject, comprising an effective amount of calcium.

19 Claims, 3 Drawing Sheets

METHODS OF ENHANCING LEAN TISSUE MASS AND BONE MINERAL CONTENT AND COMPOSITIONS THEREFOR

BACKGROUND OF THE INVENTION

1. Field of the Invention

This invention relates generally to a method of enhancing lean tissue mass in a subject by administering to the subject calcium, and optionally vitamin D. In another embodiment, the present invention relates to a method of enhancing bone mineral content in a physically active subject by administering to the subject calcium, and optionally vitamin D.

2. Background Art

One of the many numerous benefits of physical activity is increased bone mineral content (BMC)/bone density. There is strong evidence that moderate levels of weight-bearing physical activity are positively correlated to increased BMC in cross-sectional (Gutin et al. "Can vigorous exercise play a role in osteoporosis prevention?" Osteoporosis Int 1992; 2:55–69) and prospective studies (Gutin et al. and Menkes et al. "Strength training increases regional bone mineral density and bone remodeling in middle-aged and older men." J Appl Physiol 1993;74:2478–2484; Nelson et al. "A one year walking program and increased dietary calcium in postmenopausal women: Effects on bone." Am J Clin Nutr 1991;53:1303–131; and Krall et al. "Walking is related to bone density and rates of bone loss." Am J Med 1994;96:20–26). The vast majority of these studies have been done with middle aged sedentary adults who are at risk for osteoporosis and other bone-related injuries (See, e.g., Gutin et al. and, Menke et al.). There is therefore little doubt that moderate activity and increases in exercise in sedentary subjects promote positive changes in bone density.

As the literature in this area has progressed, investigators have also begun to investigate the relationship between BMC and consistent, vigorous activity. Much of the work in this area has focused on female athletes and activity-induced amenorrhoea. In these investigations, studies typically find a negative or no relationship between physical activity and BMC in female amenorrheic athletes. (Suominen H. "Bone mineral density and long term exercise: An overview of cross-sectional athlete studies." Sports Med 1993; 16:316–330 and Marcus et al. "The role of physical activity in bone mass regulation". Advances Sports Med Fitness 1988;1:63–82). The mechanism presumed to be responsible for the lowered BMC of highly trained female athletes is a low level of endogenous estrogen. (Suominen H.)

Most recently, however, there have been reports of lowered BMC/bone densities in highly trained male athletes as well. (Bilanin et al. "Lower vertebral bone density in male long distance runners." Med Sci Sports Exer 1989;21:66–70; MacDougall et al. "Relationship among running mileage, bone density, and serum testosterone in male runners." J Applied Physiol 1992;73: 1165–1170; Hetland et al. "Low bone mass and high bone turnover in male long distance runners." J Clin Endocrinol Metab 1993;77:770–775; and Rico et al. "Body composition in postpubertal boy cyclists." J Sports Med Phys Fitness 1993;3:278–281). One study (Hetland et al.) reported a negative correlation between weekly distance run and bone mineral density at several sites in male long distance runners. Bone turnover parameters were 20–30% higher in the elite runners. Because sex hormone metabolism is thought to be associated with bone density in female athletes, this was assessed in this sample of males but found to be unrelated to running activity. This study did not exclude the possibility that the lower bone density content of elite runners versus non-runners was attributable to the lower body weight of the elite runners. Additionally, there is some evidence that risk of BMC loss may be particularly high in late adolescence when bone formation is likely to be still occurring. (Rico et al.) In a study of amateur male bicyclists 15–19 years of age engaged in training that could not be described as intense (mean training=10 hours per week), total BMC and bone density were significantly lower than in sedentary controls. Because low bone density is an etiologic factor for stress fractures in athletes (Myburgh et al. "Low bone density is an etiologic factor for stress fractures in athletes." Ann Intem Med 1990;113:754–759) and stress fractures are extremely common in athletic sports (Johnson et al. "Stress fractures of the femoral shaft in athletes—More common than expected: A new clinical test." Am J Sports Med 1994;22:248–256), any reductions in BMC should be viewed with concern. Indeed, one should be observing increases in bone density in early and late adolescent athletes as this is a time of rapid bone formation. (Matkovic et al "Factors that influence bone mass formation: A study of calcium balance and the inheritance of bone mass in adolescent females." Am J Clin Nutr 1990;52:878–888.)

This phenomenon of lower bone mineral content in physically active individuals had not previously been correlated with calcium intake or calcium loss. For example, Hetland et al. concluded from their investigations that calcium consumption had no significant influence in their results which showed a negative correlation between the extent of exercise and bone mineral content.

Another benefit of certain intensity levels of and/or duration levels of physical activity is an increase in lean tissue mass (i.e. muscle). Some individuals, however, suffer decreased lean tissue mass as a result of a number of factors, including extremely high intensity levels of and/or high duration levels of physical activity. However, no relationship between decreasing lean tissue mass loss or improving lean tissue mass increase and calcium has been previously studied or established.

There exists a need in the art, therefore, to solve the problem of a lower bone mineral content associated with physical activity. There also exists a need to enhance lean tissue mass, preferably in physically active individuals.

This invention solves the problem of the prior art by providing a method to enhance the bone mineral content in physically active individuals by either decreasing a loss of bone mineral content in physically active individuals or optimally, to increase the bone mineral content of physically active individuals, by administering to those individuals calcium. This invention also provides a method of either decreasing a loss of lean tissue mass in preferably physically active individuals or optimally, to increase the lean tissue mass of preferably physically active individuals, by administering to those individuals calcium.

SUMMARY OF THE INVENTION

In accordance with the purpose(s) of this invention, as embodied and broadly described herein, this invention, in one aspect relates to a method of enhancing lean tissue mass in a subject comprising administering an effective amount of calcium to the subject, thereby enhancing the lean tissue mass in the subject.

The invention further provides a method of enhancing bone mineral content in a physically active subject comprising administering an effective amount of calcium to the subject, thereby enhancing the bone mineral content in the subject.

In another aspect, the invention provides a method of enhancing bone mineral content and enhancing lean tissue mass in a subject comprising administering an effective amount of calcium to the subject, thereby enhancing the bone mineral content and the lean tissue mass in the subject.

In yet another aspect, the invention provides a milk-free composition to enhance bone mineral content and/or to enhance lean tissue mass in a physically active subject, comprising an effective amount of calcium to enhance the bone mineral content and/or the lean tissue mass in the subject, the composition being milk-free.

In one embodiment of the invention, it was determined that there are negative changes in the bone mineral content of individual athletes as a result of physical activity, including, in one embodiment, intense training. Further evaluated was calcium loss in these exercising individuals which the invention hypothesized as one possible mechanism of action of the negative changes in bone mineral content in these same athletes. The magnitude of calcium loss in both sweat and urine during intense training was determined and both calcium intake and calcium loss through perspiration were correlated to changes in bone mineral content. Calcium supplements administered to exercising individuals decreased the rate of bone mineral content loss and, in fact, resulted in an increase in bone mineral content as well as an increase in the lean tissue muscle mass in these athletes compared to those athletes that did not take calcium supplements.

In one embodiment of the invention, the correlation between physical activity and calcium loss had not previously been recognized as an important factor in lean tissue growth and bone mineral content loss. This discovery has important implications to physically active individuals since those individuals may be experiencing lean tissue mass loss and bone mineral content loss as a result of their activity and coinciding calcium loss.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

DETAILED DESCRIPTION OF THE INVENTION

The present invention may be understood more readily by reference to the following detailed description of preferred embodiments of the invention and the Example included therein and to the Figures and their previous and following description.

Before the present methods and compositions are disclosed and described, it is to be understood that this invention is not limited to specific methods or other specific compositions, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a carbohydrate" includes multiple carbohydrates.

In one aspect, the present invention relates to a method of enhancing lean tissue mass in a subject comprising administering an effective amount of calcium to the subject, thereby enhancing the lean tissue mass in the subject.

The invention further provides a method of enhancing bone mineral content in a physically active subject comprising administering an effective amount of calcium to the subject, thereby enhancing the bone mineral content in the subject. Preferably, the subject is in need of calcium due to a calcium deficit from the physical activity.

In another aspect, the invention provides a method of enhancing bone mineral content and enhancing lean tissue mass in a subject comprising administering an effective amount of calcium to the subject, thereby enhancing the bone mineral content and the lean tissue mass in the subject.

In yet another aspect, the invention provides a milk-free composition to enhance bone mineral content and/or to enhance lean tissue mass in a physically active subject, comprising an effective amount of calcium to enhance the bone mineral content and/or the lean tissue mass in the subject wherein the composition is milk-free.

Lean tissue mass refers to non-fat soft tissues, primarily muscle tissue. Therefore, the term lean tissue as used herein specifically refers to muscle tissue in an individual. As provided in the Example section contained herein, this lean tissue, or muscle tissue, can readily be distinguished from bone material and fat tissues. Not wishing to be bound by theory, it is believed that a physically active individual who is losing more calcium as a result of their activity than they are consuming in a readily absorbable form, may be experiencing a mobilization or resorption of calcium from their bone materials to maintain their plasma calcium levels. As a result of this calcium resorption, parathyroid hormone may be secreted from the parathyroid gland, resulting in muscle weakness and atrophy. Where an individual is losing calcium as a result of their physical activity, such as through perspiration, the administration of calcium is believed to help maintain an acceptable level of calcium in the blood, thereby obviating the need for calcium resorption from bone, and thereby preventing muscle weakness and, in fact, strengthening muscles.

Bone mineral content, as used herein, refers to bone mass and is so easily correlated to bone mineral density which adjusts for bone surface area that these terms are used synonymously. Bone mineral content encompasses, but is not limited to, building bone mass while maintaining a specific bone density and building bone mass with a concurrent increase of the bone density. For example, an individual still capable of building bone or experiencing bone growth who is experiencing a decrease in their bone mineral content as a result of their physical activity may, by being administered a composition comprising calcium as provided by the present invention, decrease this loss of bone density and preferably increase their bone growth or increase their bone density, or both. Alternatively, an individual who is physically past the growth phase of growing bone, such as postmenopausal women, who are experiencing a decrease in their bone mineral content, may, for example, decrease this loss of bone density and preferably increase the density of their existing bones by being administered a composition comprising calcium, as provided by the present invention.

The term "enhance" is a term familiar to one of ordinary skill in the art and is used herein to describe either a decrease in a loss, halting of a loss, or a net increase. For example, in an individual who is still capable of growing bone, that individual may increase the growth of their bone and thereby enhance their bone mineral content by being administered calcium. Alternatively, if an individual is losing bone mineral content as a result of calcium loss due to their physical activity, that individual may be able to decrease, halt, or preferably reverse this loss by being administered calcium with an end effect of less of a loss in their bone mineral content, maintaining their previous bone mineral content by halting any bone mineral content loss, or preferably increasing their bone mineral content, thereby maximizing, or enhancing their bone mineral content.

In an individual that is no longer capable of growing bone, enhancing the bone mineral content of these individuals refers to either decreasing any bone mineral content loss, or halting any bone mineral content loss. The end result of this administration of calcium to these individuals, therefore, is decreasing any loss of bone mineral content, or preferably, maintaining their previous bone mineral content, thereby maximizing their bone mineral content.

The term "enhance" when used in reference to lean tissue mass also is a term familiar to one of ordinary skill in the art and is used herein to describe a decrease in a loss, halting of a loss, or a net increase. For example, in an individual who is capable of increasing their lean tissue mass, that individual may increase the accumulation of their lean tissue mass even above that accumulation caused by, for example, physical activity alone, and thereby enhance their lean tissue mass by being administered calcium. Alternatively, if an individual has a condition that causes lean tissue loss or participates in physical activities to such an extent that the individual actually loses lean tissue, that individual may decrease, halt, or optimally reverse this loss by being administered calcium with a net effect of less of a loss in their lean tissue mass, maintaining their previous lean tissue mass by halting any lean tissue loss, or preferably increasing their lean tissue mass, thereby maximizing, or enhancing their lean tissue mass. Enhanced lean tissue mass, by administration of calcium by the methods of this invention, also includes, for physically active individuals who may increase their lean tissue mass through exercise alone, an increase over that amount induced by exercise alone. That is, by practicing the method of this invention, physically active individuals can achieve a greater increase in their lean tissue mass with calcium intake over that amount of lean tissue increase without calcium intake.

The term subject refers preferably to mammals, more preferably humans.

The terms "physical activity" or "physically active" are also familiar to one of ordinary skill in the art and are used herein to describe a preferable minimal level of activity intensity and duration equal to a sustained continuous aerobic physical activity of at least 20 total minutes per week.

The physical activity can be at an aerobic intensity or at the higher intensity of anaerobic activity. Preferably, the aerobic activity is at an intensity of from 50%, 55%, 60%, or 70%, to 60%, 70%, 80%, 85%, or 90% of the maximum heart rate for that age subject. When an individual exceeds their aerobic capacity as a result of the high intensity of their physical activity (by definition, a higher intensity than aerobic activity), that individual has entered a metabolic state where the oxygen supply to that individual's cells is inadequate and the cell is at least partially metabolically anerobic. Those individuals that are physically active to the extent that they have exceeded their aerobic capacity and are partially anerobic will also benefit from the methods and compositions of the present invention since those individuals may also be losing calcium to a greater extent that their calcium intake, or their calcium intake is inadequate, and those individuals are losing bone mineral content and/or losing lean tissue mass and /or not accumulating lean tissue mass to the extent they would if their calcium levels were adequate.

In one embodiment, the total time of the physical activity per week is at least 40 minutes. In another embodiment, the total time of the physical activity per week is at least 80 minutes. In another embodiment, the total time of the physical activity per week is at least 160 minutes. In another embodiment, the total time of the physical activity per week is at least 320 minutes. In another embodiment, the total time of the physical activity per week is at least 500 minutes. In another embodiment, the total time of the physical activity per week is at least 1000 minutes. This physical activity does not have to occur at any one occurrence and may be a single session or divided into multiple sessions. Preferably, each session duration is at least 20 minutes.

The specific activity that describes a physical activity that an individual participates in will, of course, vary, and an individual may participate on one or more of these activities. For example, an individual may participate in activities, including but not limited to, jogging, running, basketball, tennis, soccer, football, walking, bicycling, rowing, racquetball, or non-sports exertions such as lawn work, heavy lifting, and the like. Thus physical activity herein denotes some minimal activity over mere sedentary activity and is preferably at least an exercising or athletic aerobic activity or even an athletic anaerobic activity. Such physical activity also includes very intense activity such as long distance and marathon running and competitive sports activity, including Olympic caliber training and competition.

An individual being administered calcium may benefit from this administration if that individual has a calcium deficit, where this deficit is not a result of their physical activity. For example, if a person has a suboptimal level of calcium in their body resulting from an inadequate intake of calcium, a non-physical activity related loss of calcium, a disease state or condition where that individual requires additional calcium for their optimal bone mineral content or lean tissue mass, that individual may enhance their bone mineral content, their lean tissue mass, or both, by being administered calcium.

It is preferred that the calcium in the calcium-containing composition be soluble so that it may be readily absorbed by the subject. The calcium in the composition may be in one or more of many forms of calcium that will be apparent to one skilled in the art. For example, the calcium may be in the form of calcium citrate, calcium carbonate, calcium malate, calcium phosphate, calcium hydroxide and mixtures thereof depending on the calcium source.

A preferred form of calcium is calcium citrate. It will be apparent to one skilled in the art that a different form of calcium may be used to add calcium to the composition and still maintain a preferred form of calcium in the composition. For example, calcium hydroxide may be mixed with citric acid to yield a composition comprising calcium citrate.

Alternatively, the calcium as used in the methods described herein can be in the form of a solid and administered to a subject in a solid form or the solid may be dissolved prior to the administration of the composition. Thus, the composition can be in the form of, for example, a solid, semi-solid, a powder, a suspension, a liquid, or any other effective form and administered to the subject as such or changed to another form prior to administration.

The calcium may be present in the composition and in the methods described herein in the form of a calcium-fortified aqueous drink. In one embodiment of the present invention, calcium is provided in the composition as calcium-fortified orange juice. For example, MINUTE MAID® calcium fortified orange juice contains 37.5 mg calcium per serving ounce and can be used as a source of calcium. Other sources of calcium are readily available from other commercial food and nutritional supplies, such as Hi-C® drinks, and one skilled in the art can readily determine which commercially available materials may supply the source of calcium.

By administration is meant any method which effectively delivers the composition comprising calcium to the subject so as to effectively enhance the bone mineral content, enhance the lean tissue mass, or both. The administration of calcium to a physically active individual may be before the physical activity, during the physical activity, or after the physical activity.

Although the methods and compositions as provided by the present invention are primarily directed toward individuals that are in need of calcium as a result of their physical activity, certain individuals may be in need of calcium not solely due to any physical exercise, but possibly because of a metabolic disorder, condition, syndrome, or because that individual has an inadequate calcium intake and those individuals may enhance their bone mineral content and/or lean tissue mass by being administered calcium. For example, individuals experiencing osteoporosis may benefit from the administration of calcium, not only to enhance their bone mineral content but their lean tissue mass. Any individual that has a deficit of calcium as a result of a particular metabolic disorder, condition, syndrome, or because of an inadequate intake of calcium, and may be losing bone mineral content or lean tissue mass, or not increasing their bone mineral content or lean tissue as a result of this calcium deficit may enhance their bone mineral content and/or lean tissue mass by being administered calcium.

The administration of the composition comprising calcium to the subject can be a single administration or multiple administrations and the total amount of calcium supplement administered to the subject may depend on other sources of calcium available to the subject, such as dietary intake, as well as other factors such as the intensity of physical activity, the perspiration rate of the subject, the duration of the physical activity, other sources of calcium loss in the individual, alcohol intake, pH of the stomach, their smoking status, age of the subject and other factors. One skilled in the art will readily appreciate that a combination of factors such as these, and others, will determine the specific dose of calcium needed to maximize lean tissue growth and/or bone mineral content in a subject.

An effective amount of calcium is defined as the amount of calcium that results in an enhanced bone mineral content or an increase in lean tissue mass, or both, in an individual depending upon the claimed method or composition. Where the composition is a liquid, the amount of the calcium in the composition is preferably from about 12 mg, 20 mg, 50 mg, 100 mg, 150 mg, or 200 mg per fluid ounce to about 20 mg, 50 mg, 100 mg, 150 mg, 200 mg or 250 mg per fluid ounce, more preferably about 37.5 mg calcium per fluid ounce of the composition. In one embodiment, the amount of calcium administered equates to a total daily dose of from about 100 mg, 250 mg, 500 mg, 750 mg, 1000 mg, 2000 mg, 3000 mg, or 3500 mg to about 250 mg, 500 mg, 750 mg, 1000 mg, 2000 mg, 3000 mg, 3500 mg, or 4000 mg per day.

Where the administration of calcium to the subject is a single administration, the concentration of the calcium in the composition can vary depending on the total amount of calcium to be administered to the subject, as well as the other factors mentioned earlier. One skilled in the art will readily determine the optimal concentration of calcium in the composition to be administered in a single administration. For example, if the calcium concentration is too dilute, the subject will then have to consume more fluid to receive the same dose as a composition where the calcium is more concentrated when delivered in the liquid form. The total amount of calcium administered will also depend on other sources of calcium, such as dietary, and the amount of calcium loss by the subject, such as through perspiration. One skilled in the art can readily determine calcium intake and calcium loss, as exemplified in the Example contained herein, to then determine the amount of calcium the subject should receive to maintain calcium homeostasis, or alternatively a net increase in calcium uptake.

In another embodiment, the present invention provides a composition comprising an effective amount of calcium and an effective amount of vitamin D and a method relating to administering such a composition. Vitamin D promotes the absorption of calcium in a subject and contributes to the regulation of plasma calcium levels. Therefore, an effective amount of vitamin D will be that amount of vitamin D which will aid in the absorption of calcium in a subject that has been administered calcium in order to enhance the lean tissue mass or the bone mineral content, or both. The current recommended daily allowance of vitamin D is at least 400 I. U. (International Units). The amount of vitamin D administered preferably equates to a total daily dose of from approximately 5 I.U. per day to subtoxic levels or to below levels that give undesired side effects. In one embodiment, the vitamin D is administered from about 5, 50, 100, 200, 400, 600, or 800 to about 600, 800, 1000, 2500, 5000 or 10000 IU per day although it is understood that higher levels can be administered because the toxic dose is much higher.

In one embodiment, the amount of the vitamin D in a liquid composition ranges from about 2.5, 5, 7.5, 10, 12.5, 15 or 20 I.U. per fluid ounce to about 10, 12.5, 15, 20, 50, 100, 1000 or 4000 I.U. per fluid ounce, the preferred concentration being about 12.5 I.U. of vitamin D per fluid ounce of the composition.

The vitamin D can be administered before, during, after, or simultaneously with the administration of calcium, and either separately or in the same composition as the calcium. Preferably, the vitamin D is administered to the subject within the same composition comprising calcium.

The specific form of vitamin D may also vary. As used herein, the term vitamin D includes, but is not limited to, vitamin D, salts of vitamin D, esters of vitamin D, acids of vitamin D, precursors of vitamin D, derivatives of vitamin D, and any other biologically form or biologically active metabolite of vitamin D, including vitamin $D_2$ and vitamin $D_3$ or mixtures thereof.

Vitamin D can be provided from any number of sources. For example, vitamin D salts can be mixed with the composition comprising calcium in either a liquid or solid form which itself can then be dissolved. A concentrated liquid vitamin D can be added to the calcium to achieve the preferred concentration of vitamin D in the composition. Alternatively, vitamin D can be obtained from any number of commercially available compositions which will be apparent to one skilled in the art. In a preferred embodiment, the source of vitamin D is CLASSIC OVALTINE®. CLASSIC OVALTINE® is a commercially available fat free powdered drink mix trademarked by Sandoz Nutrition Corp. and distributed by Himmel Nutrition Inc., Hypoluxo, Fla. 33462, USA, comprising the following components: sugar, cocoa processed with alkali, barley malt extract, sweet dairy whey, beet extract, salt, mono and diglycerides, molasses, natural caramel flavor, and vanillin, and having the following nutritional facts: 115 mg sodium, 18 g total carbohydrate (less than 1 g dietary fiber and having 15 g sugars), 1 g protein, and the following minerals and vitamins based on a percent daily values for a 2000 calorie diet; vitamin A 45%, vitamin C 45%, calcium 8%, iron 15%, vitamin D 50%, vitamin B-1 60%, vitamin B-2 45%, niacin 45%, vitamin B-6 45%, and phosphorus 8% per serving size (21 grams).

In another embodiment the present invention also provides a milk-free composition comprising calcium, even more preferably such a composition that is lactose-free and fat-free. Milk products have traditionally been an important source of calcium, but milk products typically contain fats and lactose. Fats are metabolized relatively slowly by individuals when compared to other energy sources, such as simple carbohydrates. In exercising individuals, or individuals that are physically active, it is important to provide those individuals with a source of energy that is readily metabolized and which, therefore, can provide a relatively direct source of energy. The composition of the present invention is preferably milk-free, and preferably does not contain fat and therefore the energy source provided by the composition, namely readily metabolized carbohydrates, provides an energy source that is readily available to the individual consuming the composition.

Many individuals are lactose intolerant and are therefore unable to metabolize lactose. The composition of the present invention also preferably provides a source of calcium to those individuals without simultaneously administering lactose to those individuals. Lactose intolerant individuals that require a supplemental source of calcium, whether through exercise or physical activity-induced calcium loss, may utilize the composition of one embodiment of the present invention without experiencing lactose intolerance-associated adverse effects.

In another embodiment, the present invention further comprises a flavorant. As used herein, the term "flavorant" includes any additive to the composition which improves the flavor, or the palatability of the composition. The exact nature of the flavorant will, of course, vary since individuals naturally have differing interpretations on what constitutes an acceptable flavor. The added flavor may be derived from natural sources such as fruits, nuts, leaves, and the like. The added flavor may also be derived from an artificial source, such as a synthetically prepared compound or compounds which provide an acceptable taste. Alternatively, the flavorant may comprise a mixture of natural and artificial flavorants or a mixture of different natural sources or a mixture of different artificial sources. For example, the flavorant may comprise an orange flavor, a berry flavor, a pineapple flavor, a lime flavor, a combination of orange and lime flavors, and so on. The source of the flavorant may also be a commercially available food product, such as a commercially available fruit juice. In a preferred embodiment of the present invention, the source of the flavorant is grenadine.

The specific amount of flavorant will also vary with the source of the flavorant since the flavor intensity will vary from source to source. An acceptable concentration of the flavorant will be apparent to one skilled in the art.

In another embodiment, the present invention further comprises a carbohydrate. One skilled in the art will readily appreciate that carbohydrates, particularly glucose and fructose, are compounds that enter metabolic pathways, such as the glycolytic pathway, to yield a net increase of ATP in a cell, which itself is a source of energy for other processes in a cell. The source of the carbohydrate may also vary. For example, the source of the carbohydrate may be glucose, fructose, sucrose, or any other mono- or disaccharide that is readily metabolized. These carbohydrates include their salt forms, their phosphorylated forms, their derivatives, and any other modifications to these carbohydrates. The amount of the carbohydrate in the composition may also vary.

The specific pH of the composition, when liquid, can also vary, but should preferably be within a range such all the components of the composition are soluble and such that the composition has no adverse effects on the subject that are attributable to the pH of the composition.

The composition of the present invention may also contain other components which will be apparent to one skilled in the art. For example, preservatives, pH buffers, vitamin D stabilizers, colorants or other additives may also be added to the composition, if desired.

The following example is put forth so as to provide those of ordinary skill in the art with a complete disclosure and description of how the methods claimed herein are utilized and evaluated, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for.

EXAMPLE

Methods

Subjects

Subjects for all three phases of this investigation were the 1993–4 and the 1994–5 members of a major Division I-A men's basketball team. At preseason during 1993–4, the average subject age was 20 years (range=18 to 22). Average height of participants was 195 cm (range=179.5 to 210.2 cm) and average weight was 85 kg (range=68.2 to 104.5 kg). All protocols for this study were approved by the University of Memphis Institutional Review Board.

Body Composition Assessment

The equipment used for assessing body composition was a Hologic QDR-2000. Dual Energy X-ray Absorptiometry has emerged as one of the best methods of assessing BMC because it is a simple and rapid test to perform, has a low radiation dose, and the accuracy of the test does not depend on hydration. (Heymsfield et al. "Appendicular skeletal muscle mass: measurement by dual-photon absorptiometry". Am J Clin Nutr 1990;52:214–218). Dual photon absorptiometry techniques and DEXA permit the body to be segmented into three components: bone, fat, and fat-free soft tissues. (Going et al. "Detection of small changes in body composition by dual-energy x-ray absorptiometry." Am J Clin Nutr 1993;57;845–850). (Kellie, S E. "Measurement of bone density with dual-energy x-ray absorptiometry" (DEXA). JAMA 1992;267:286–294). Because one of the concerns about DEXA technology is lack of standardization, (Roubenoff et al. "Use of dual-energy x-ray absorptiometry in body composition studies": Not yet a "gold standard". Am J Clin Nutr 1993;58:589–591) careful quality control, standardization, and calibration procedures were followed. The DEXA technologist was trained by the manufacturer and is licensed by the American Registry of Radiologic Technologists (ARRT). The Hologic system used in this study was calibrated daily against a spinal phantom in the AP/lateral and single beam modes to ensure no systematic deviations. Every pixel is calibrated against a tissue bar phantom to determine if the pixel is reading bone, fat, lean tissue, or air. After performing the Quality Control (QC) scans, the information from the scans are then entered into the QC database and monitored for the life of the unit. This close tolerance produces an extremely low error rate with the coefficient of variation for this machine (n>100) being 0.47%.

Test-retest reliability on actual subjects was measured by conducting serial DEXAs on 14 athletes (Division I-A baseball players) taken approximately 30 minutes apart. Both intra-operator (n=4) and inter-operator (n=10) reliability were assessed and found to be equivalent. Mean deviation for total BMC, leg BMC, total body lean tissue, and leg lean tissue averaged 0.31% and the mean intra-class correlation (ICC) was 0.985.

The head region was excluded in all BMC analyses per Hologic protocol since this is an assumed, not a derived value. Initially, analyses were conducted for both BMC and density. Results for change over time were very similar with both methods. Because both BMC and bone mineral density are reported in the physical activity literature and because both measures predict health outcomes (e.g., fractures, osteoporosis) equally well, (Cummings et al. "Bone mass measurement and risk of fracture in Caucasian women: A review of findings from prospective studies." Am J Med 1995;98 (Suppl 2A):245–285) only BMC is reported to avoid redundancy.

Phase I Procedure: Prospective Study of Bone Mineral Content Over a 1 year Period Team members had body composition measured by a DEXA test one month before formal practices were allowed (September), at midseason following the 14th (of 28) regular season game (early January), approximately three weeks after the final season game (late March), and again in the late summer (mid July). This team trains year round except in March and April (when postseason DEXAs were performed).

Overall differences among BMC for the total body and legs over the four assessment periods were assessed using one-way repeated measures analysis of variance. F-statistics were corrected for sphericity using the Greenhouse-Geisser epsilon. Follow-up testing consisted of single degree of freedom contrasts which evaluated serial changes in BMC (i.e., pre- to midseason, mid- to post-season, and post-season to summer) as well as overall change from preseason to summer. All analyses were conducted using the Statistical Analysis System (SAS Institute, Cary, N.C.).

Phase II Procedure: Calcium Loss and Change in BMC During Short-term Intense Training Formal training commenced in mid-July, 1994, as the team began preparing for a foreign, summer tour. For 10 days, the team practiced on average two times a day. Each training session was in excess of 2 hours. Practice included a variety of intensive offensive and defensive drills. Full-court practice games ("scrimmages") occurred approximately every other day except for the last day which was shorter and much less intense.

The practice environment was an indoor, non-air conditioned gym. The training environment was very hot and humid (mean temperature=30.3° C.; mean % humidity= 62.5%). Collection of sweat in a field setting followed the procedure as described by (Tipton et al. "Zinc loss in sweat of athletes exercising in hot and neutral temperatures." Int J Sport Nutr 1993;3:261–271). Three times during the 10 day practice period, each player was given a specially treated, 100% cotton t-shirt that he wore under his jersey. Prior to putting on the t-shirt, it was washed in distilled water. Each athlete wore this shirt for the first hour of practice. The shirt was then removed by a research assistant with gloves and placed in a sterile plastic container. Shirts were taken to a training room where the sweat was extracted using a funnel and a vial. All samples were coded and refrigerated.

To estimate sweat loss, all subjects were weighed without their jerseys and the treated t-shirts before and after practice, using a highly sensitive, digital scale. Fluid intake was adjusted by having individual bottles of water for each player. All fluid intake was recorded and used to adjust for total sweat loss. After practice, total urines were collected. Volume of urine was used to determine urinary calcium concentration and loss.

Measurements

Determination of Calcium Concentration and Loss in Urine and Sweat

Samples of sweat and urine were analyzed at Baptist Regional Laboratories, Memphis, Tenn., using Inductively Coupled Plasma Mass Spectrometry (ICP-MS) with an Elain 5000 ICP-MS (Perkin Elmer Corp., Foster City, Calif.). This method is a standard procedure for determination of multi-elements in urine, (Voellkopf et al. "Rapid multi-element analysis of urine." Atomic Spectroscopy 1995; 16:19–21) and it was adopted for measurements of calcium in sweat. For quality control, five pairs of sweat duplicates were sent to the laboratory for calcium analysis. The mean difference between duplicate samples was −3.2±3.1 mg/l. The pairs were highly correlated (r=0.96, p=0.008) and did not significantly differ from each other (t[4]=2.30).

Calcium Intake

Calcium intake during the training period was assessed by the rapid assessment method (RAM). (Hertzler et al. "A dietary calcium rapid assessment method (RAM)." Topics in Clin Nutr 1994;9:76–85). The RAM was developed for use with adolescents and has been shown to compare well to dietary recalls and records. This measure originally had 27 items and foods fortified with calcium were added which have recently come on the market (orange juice, bread, and fruit-flavored drinks). The RAM covers short-term intake (e.g., one week). Each measure was interviewer-administered and food models illustrating serving sizes were displayed.

Finally, BMC was assessed on the first and last day of the 10 day training period using the same DEXA equipment and procedure as outlined in Phase I. The relationship of dietary calcium intake to BMC was assessed by Pearson correlations and two-sample t-tests which compared BMC change according to whether calcium intake was below or above 2000 mg/day.

Phase III Procedure: Intervention with Calcium Supplementation

Subjects were eleven subjects of the Division I-A basketball team who participated in Phase I. Intervention commenced the week prior to the fall training season (Oct. 1, 1995) and continued through postseason play (i.e., the NCAA tournament, March, 1996). Given the large decreases in BMC that were observed in Phase II from preseason to midseason (see FIG. 1), intervention was most aggressive from preseason to midseason. DEXA assessments, using the equipment and protocol described in Phase I, were conducted prior to the beginning of the season, at midseason (at the same time as midseason DEXAs the previous year), and approximately one month after postseason play. Urinary calcium/creatinine ratios were determined on all supplemented players to determine if the increased calcium intake placed any subjects at risk for kidney stones (none became at risk). Dosage of oral calcium and vitamin D was determined by the pattern of BMC change observed during year 1. A dosage algorithm was developed based on consideration of the usual level of calcium intake observed among adolescents and collegiate athletes, the therapeutic dosages of calcium (ranging from 500–2000 mg per day) which have produced positive effects on bone mass in clinical trials of adolescents and post-menopausal women, (*National Institutes of Health*, "Optimal Calcium Intake: NIH Concensus Development Conference Program and Abstracts." Bethesda, Md.: NIH Press; 1994) and recommended maximum calcium intake levels to prevent toxicity. (*National Institutes of Health*) The algorithm used was as follows: 1) Those players who lost ≧2% of BMC from the whole body or either leg from pre-season to mid-season and continued to lose at post-season received 1800 mg calcium/400 I.U. Vitamin D plus Tigers Thirst Quencher drink (Formula TTQ; described below); 2) Those who lost ≧2% of BMC from the whole body or either leg from pre-season to mid-season, but increased from mid-season to post-season, received 1000 mg calcium/400 I.U. Vitamin D plus Formula TTQ; and 3) Those who lost <2% of BMC from the whole body or either leg from pre-season to mid-season (n=3) did not receive oral supplements, but were encouraged to regularly drink Formula TTQ.

A major goal of the intervention was to increase dietary calcium as well. The primary sources of calcium in the diet are dairy products, and a very high percentage of African Americans are lactose intolerant (Scrimshaw et al. "The acceptability of milk and milk products in populations with a high prevalence of lactose maldigestion." Am J Clin Nutr 1988;48:1086–1098). Formula TTQ was designed as a non-dairy calcium and Vitamin D-rich drink combined from readily available commercial food stuffs. This drink, per liter, provided as much calcium and Vitamin D as milk. Formula TTQ is made from 12 ounces of MINUTE MAID® calcium fortified orange juice combined with 2 dry ounces Classic Ovaltine®, 1.67 fluid ounces of grenadine and 36 fluid ounces of water. This formula was available for consumption at every practice (practices averaged 6 days per week) and prior to every home game. All subjects were encouraged to drink at least two, 240 ml cups of the drink per day, which would supply 600 mg of calcium and 160 I.U. of Vitamin D. Consumption averaged 7.6 liters per day for the team or approximately 0.5 liters for each player.

Changes in BMC from preseason to midseason the first year (Phase I) were compared to changes in BMC from preseason to midseason the second year by one-way repeated measures ANOVA. Similarly, changes in BMC from midseason to postseason between Years 1 and 2 were compared. It is important to note that all subjects served as their own controls in this intervention phase: Phase I served as a baseline year while Phase III assessed the effects of calcium supplementation on the same subjects. Given that calcium is needed for lean body mass development, (Williams, M H, "Vitamin supplementation and athletic performance." Int J Vitam Nutr Res Supp. 1989;30:163–91) we also investigated potential changes in lean tissue (as measured by DEXA) over the 2 year period as well.

Results

Phase 1: Changes in BMC Over Time

Figure 1:
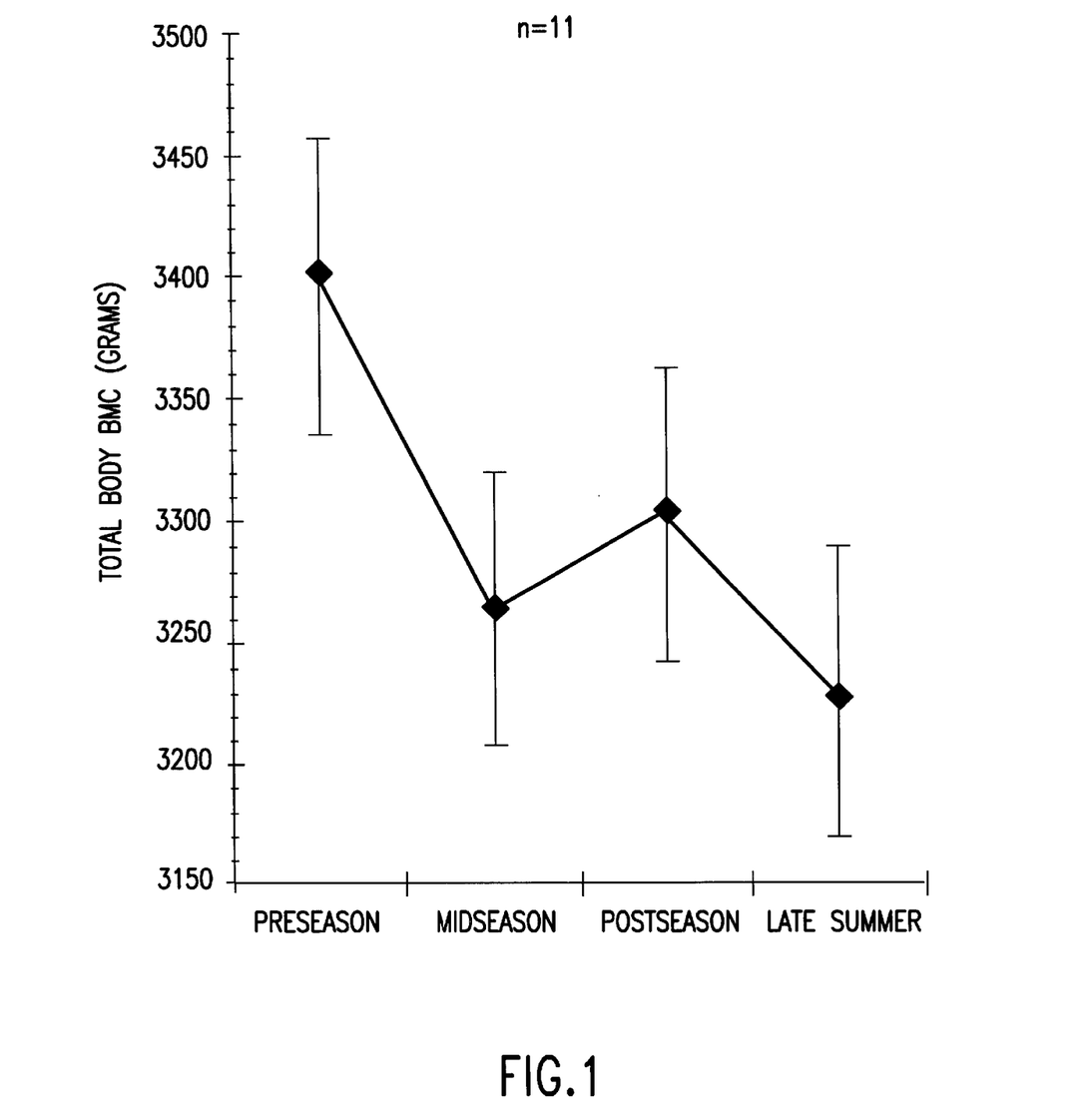
FIG. 1 shows bone mineral content (mean±standard error) of the total body in Division I-A collegiate basketball players over one year.

Preseason, midseason, postseason, and summer values for total BMC are presented in FIG. 1. Across the four assessment periods, significant differences in BMC were observed for both the total body [$F(3,30)=9.35$, $p=0.0015$] and the legs [$F(3,30)=14.73$, $p<0.0001$]. As indicated in FIG. 1, total BMC significantly decreased from preseason to midseason. While there was considerable variability among players, total BMC dropped by 3.8% over this relatively short period of time (mean=−133.4 g; 95% confidence interval [C. I.]=−231.2−35.6; $p=0.0234$). BMC among individual players ranged from an increase of 3.9% to a decrease of 13.4%.

From midseason to postseason, total BMC did not change significantly (mean=35 g; 95% C. I.=−17.0−87.6, p.=0.21) and was marginally lower (2.8%) than preseason values (mean=−98.1 g; 95% C. I.=−196.0−0.2, $p=0.07$). Although BMC stabilized from mid to postseason (corresponding with a temporary stopping of playing and practicing), values dropped precipitously when playing resumed in early summer. From postseason to summer there was another decrease of 3.3% in total BMC (mean 113.1 g; 95% C. I=0.187.5−38.4, $p=0.01$). Total BMC change among individual players ranged from an increase of 1.1% to a decrease of 10.1%. From preseason to late summer (10 months), there was an overall decrease of 6.1% in total BMC (mean=−211.2 g; 95% C. I.=−303.7−118.7, $p=0.001$).

Changes in BMC of the legs paralleled changes observed for the whole body. A decrease of 6.0% occurred from pre- to midseason (mean=−53.5 g; 95% C. I.=−88.4−18.6, $p=0.01$). There was a slight rebound at postseason, but values were still 4.9% below preseason (mean=−44.6 g; 95% C. I.=−79.4−9.8, $p=0.03$). Values decreased again during the summer when practices resumed. By late summer, BMC of the legs was 10.5% below preseason (mean=−91.8 g; 95% C. I.=−126.2−57.3, $p=0.0002$). Among individual players, change in leg BMC across the entire year (from preseason to late summer) ranged from a decrease of 2.2% to 20.2%.

Finally, it should be noted that preseason, midseason, and postseason BMC values were available for three additional players who did not return for the 1994–95 season. Including these players in the analyses did not alter the patterns of change.

Phase II: Determination of Calcium Loss During Short-term Intense Training

Table 1 below presents the means and standard deviations of the relevant variables in this investigation. Calcium loss was estimated as a function of total fluid loss (determined by weight loss and adjusted for fluid replaced), and calcium concentration in sweat. As can be seen in Table 1, average weight loss per training session averaged 2.13 kg (SD=0.32) with a daily range from 0.17 to 4.37 kg. Mean loss of calcium from sweat across the three days of training averaged 422 mg (SD=308−2). Inspection of Table 1 shows that both calcium concentration and estimated total loss from sweat decreased over time. In contrast to the sweat results, the urinary calcium loss was minimal (mean 4.7 mg, SD=3.1), primarily due to very low urinary output during training (mean over 3 days=46.9 ml±17.6). Consistent with other findings, (Chu et al.) no compensatory decrease in urinary excretion occurred over time. However, there was a tendency for urinary concentration to increase over time.

Neither total nor leg BMC changed during this short-term intense training.

Figure 2:
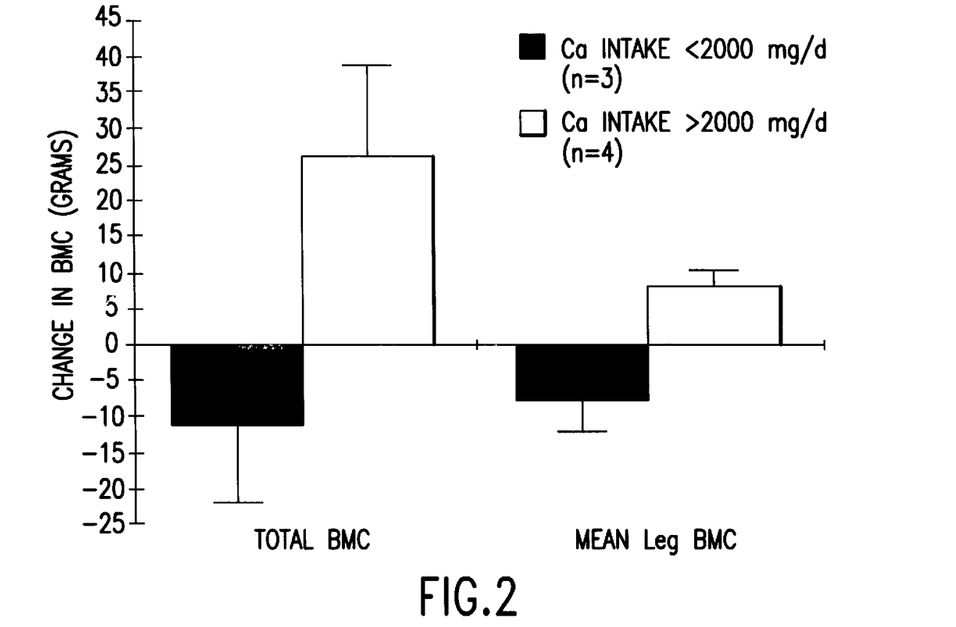
FIG. 2 shows changes in bone mineral content (mean±standard error) during athletic training according to calcium intake.

Dietary calcium intake was strongly related to changes in total BMC (r=0.69, p=0.0876) and mean leg BMC (r=0.89, p=0.0077). As can be seen in FIG. 2, dietary calcium intake of the median of 2000 mg or more during intense training was associated with increases in BMC for the total body and legs. In contrast, dietary calcium intake of less than 2000 mg was associated with decrease in BMC for the total body and legs. For the total body, subjects with calcium intake of less than 2000 mg dropped an average of 11.2 g of BMC, while subjects with calcium intakes of 2000 mg or more increased an average of 26.0 g of BMC [t(5)=2.19, p=0.0798]. Similarly, leg BMC decreased by 9.7 g for those with calcium intake below 2000 mg, and increased by 6.4 g for those with intake of at least 2000 mg [t(5)=4.41, p=0.0070].

TABLE 1

Means and Standard Deviations (±) for the Major Variables of Investigation

|  | Day 1 | Day 2 | Day 3 | Mean | P Value for Linear Trend |
|---|---|---|---|---|---|
| Average corrected weight loss (kg) per training session (n = 9) | 2.76 ± 0.77 | 2.36 ± 1.18 | 1.31 ± 0.82 | 2.13 ± 0.32 | 0.004 |
| Sweat calcium concentration (mg/l) (n = 10) | 81.4 ± 40.8 | 57.7 ± 24.4 | 55.6 ± 37.6 | 64.9 ± 30.8 | 0.030 |
| Estimated calcium loss in sweat (mg/training session) (n = 9) | 624.4 ± 641.0 | 462.3 ± 521.2 | 179.2 ± 92.2 | 422.0 ± 308.2 | 0.080 |
| Urinary calcium concentration (mg/l) (n = 9) | 73.6 ± 58.0 | 56.1 ± 30.9 | 128.2 ± 30.9 | 86.0 ± 39.4 | 0.070 |
| Estimated calcium loss in urine (mg/training session) (n = 9) | 4.6 ± 6.0 | 3.2 ± 2.4 | 6.2 ± 5.0 | 4.7 ± 3.1 | 0.500 |
| Dietary calcium intake (mg) (n = 9) |  |  |  | 2013.7 ± 879.4 |  |

Phase III: Intervention with Calcium Supplements

Figure 3:
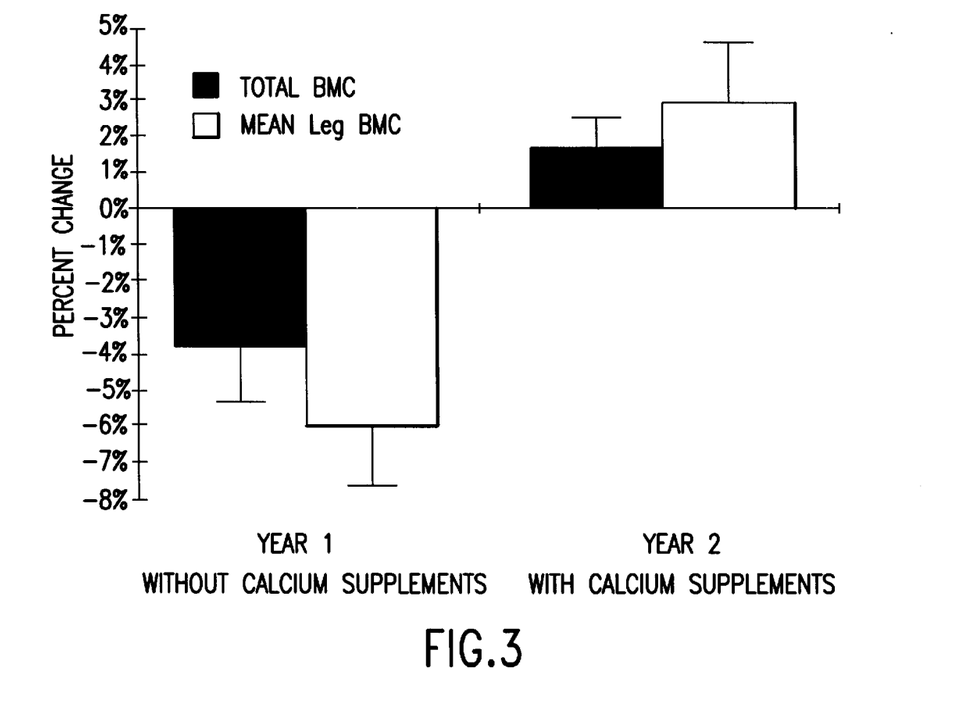
FIG. 3 shows pre- to midseason percent change in total and leg bone mineral content as a function of calcium supplementation.

Changes in BMC from preseason to midseason for both years (one without calcium supplementation, one with calcium supplementation) are presented in FIG. 3. As can be seen in FIG. 3, total BMC dropped approximately 3.8% from preseason to midseason the first year while BMC in the legs (where stress fractures in many athletes occur) decreased 6%. As also can be seen from the figure, calcium supplementation was associated with a marked increase in BMC. In the second year with supplements, total BMC increased almost 2% (mean 52.1 g; 95% C. I.=9.3–94.9, p=0.038) and leg BMC increased almost 3% (mean=21.2 g; 95% C. I.=2.5–39.9, p=0.05). Comparing the changes in BMC between Seasons 1 and 2, statistically significant differences for both total BMC (mean=185.5 g; 95% C. I.=94.9–276.01, p=0.002) and leg BMC (mean=74.6 g, 95% C. I.=41.4–107.8, p.001) were observed.

In terms of BMC changes from midseason to postseason, DEXA assessments were conducted approximately one month after postseason play on seven available players. From mid-season to post-season total BMC continued to increase, another 1.1% for total BMC (mean=36.2 g; 95% C. I.=6.8–65.6, p=0.05) and another 1.6% for leg BMC (mean= 12.6 g; 95% C. I.=4.5–20.7, p=0.02).

Figure 4:
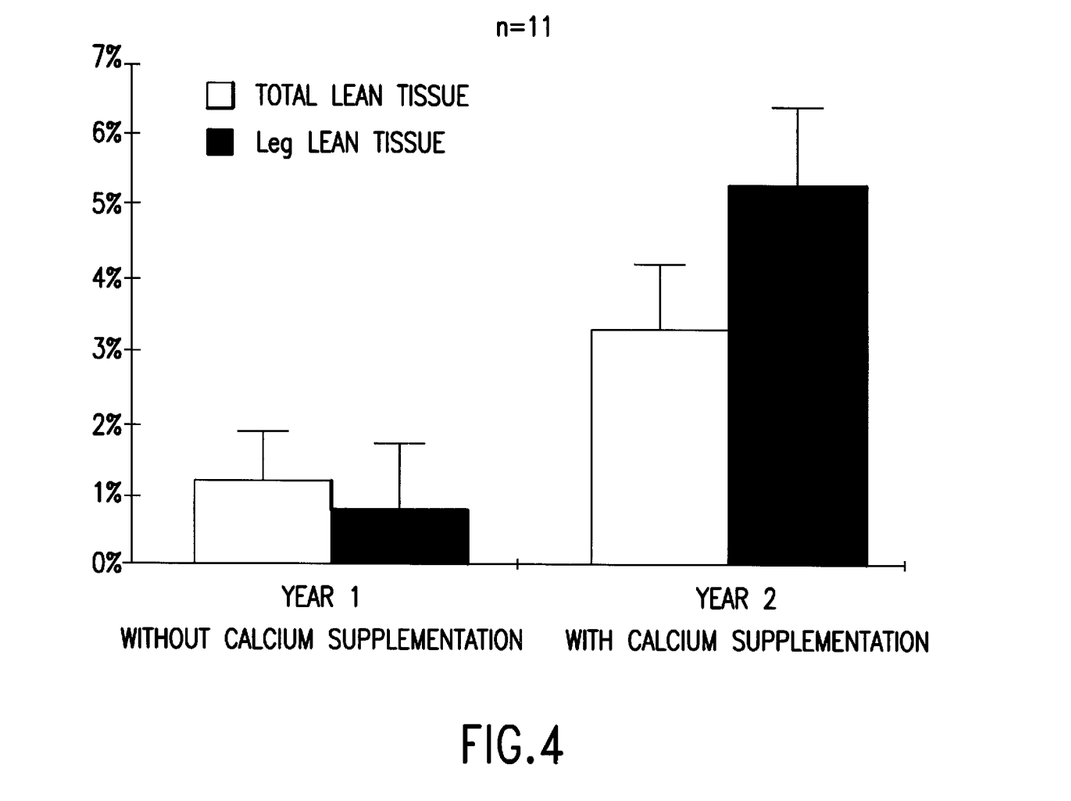
FIG. 4 shows pre- to midseason percent change (mean±standard error) in total and leg lean tissue as a function of calcium supplementation.

Changes in lean tissue from preseason to midseason for both years are presented in FIG. 4. Lean tissue changed surprisingly little (given the amount of training) from preseason to midseason in the first year. Lean tissue mass increased 1.2% overall, and most of this increase was observed in the trunk region (3.2%). Lean tissue in the legs did not change significantly (mean=73.3 g; 95% C. I.=–207.0–353.6, p=0.62) representing an increase of only 0.8% from preseason to midseason the first year. In marked contrast to the first year, calcium supplementation was associated with marked increases in lean tissue, both in terms of total lean tissue increase (3.2%, mean=2123.4; 95% C. I.=1249.8–3015.0, p=0.0008) and lean tissue increase in the leg region (5.2%, mean=622.7; 95% C. I.=425.7–819.7, p<0.0001). Comparing the changes in lean tissue between years 1 and 2 indicated statistically significant differences for leg lean mass (mean=549.4; 95% C. I.=264.5–834.3), p=0.003) and a marginally significant difference for total body lean mass (mean=1360.0; 95% C. I.=115.6–2604.0, p=0.58).

The results of the current investigation indicate, inter alia, three major findings. The first is that at least some athletes (those who train intensely for long periods of time) may be at risk for decreases in BMC. This is the first prospective study to document negative changes in BMC during training and is consistent with a growing cross-sectional literature that suggests that very intense levels of physical activity is related to decreases in BMC in both men and women. (Suominen et al., Bilanin et al., and Rico et al.) Given that low bone density is an etiologic factor for stress fractures in athletes, (Gutin et al.) the current findings may partially explain the high incidence rates of stress fractures in some sports.

A second major finding is that a fairly large amount of calcium is lost in sweat during intense training. Calcium loss averaged 422 mg per training session, although loss decreased over time. Whereas previous studies produced an estimate of calcium loss during either resting or short bouts of moderate exercise, the current study found much larger losses of dermal loss of calcium in athletes during prolonged, intense exercise. To our knowledge, this is the first investigation that estimated calcium loss in highly competitive athletes while they were training. Additionally, calcium intake was positively associated with changes in BMC and although the sample size was small, results suggested that a calcium intake of approximately 2000 mg/day may be necessary to promote BMC, at least during training this intense.

It should come as no surprise that the estimated calcium loss through sweat is much higher in this study compared with others given the intensity and duration of the training as well as the climate conditions. However, other studies did not typically exercise subjects at all (Charles et al., Dermal, intestinal, and renal obligatory losses of calcium: relation to skeletal calcium loss. Am J Clin Nutr 1991;54:266S–272S). During intense training, whether it be collegiate athletes engaged in basketball training or other endurance-type Olympic events, levels of energy expenditure are extremely high for prolonged periods of time. Given the extant literature and the types of intense training that have evolved over the past 20 years, it appears that calcium needs during intense exercise have been underestimated.

It is interesting to note that calcium concentration and estimated loss in sweat decreased over time, indicating, perhaps, a physiological adaptation to the large amounts of calcium being lost. Over a 10 day training period, sweat calcium concentration decreased approximately 32%. While estimated calcium loss decreased more over this 10 day period, this large change may be misleading because training was relatively light on the last day. Although one could argue that total calcium loss could be a function of a less intense training schedule, a lighter training schedule would not explain the decreases in calcium concentration (mg/l). This adaptation to loss of a vital mineral is consistent with other literature that suggest, for example, the amount of sodium loss in sweat decreases with prolonged training. (Kirbv et al. "Plasma aidosterone and sweat sodium concentration after exercise and heat acclimation." J Appl Physiol 1986, 61:969–70).

The third major finding from the current investigation was that onset of calcium supplementation was associated with increases in BMC during a period of time (preseason to midseason) where we previously observed decreases in BMC in the same athletes. From midseason to postseason, BMC continued to increase. This study, using subjects as their own control, indicates the potential role of calcium supplementation increases in BMC during intense training. The combined observations that (a) decreased BMC was observed over a 1 year period; (b) these athletes were observed losing large amounts of dermal calcium during training; and (c) calcium supplementation was associated with increased BMC in these same athletes, strongly suggests increased calcium needs during intense training beyond standard RDA recommendations. This set of findings may also help reconcile previous contradictory findings on the role of intense exercise on BMC in that it appears that exercise may promote BMC provided calcium intake is sufficiently high to overcome the dermal loss of calcium during training.

The increases in lean tissue observed during calcium supplementation is a potentially important finding. The negative calcium balance that most likely occurred in our athletes could have stimulated parathyroid hormone (PTH) secretion. It is known that muscle weakness and histological changes with myopathy occur in hyperparathyroidism. (Patten et al. "Neuromuscular disease in primary hyperparathyroidism." Ann Int Med 1974;80:182–193). Thus, the positive effect of calcium supplementation on bone and lean body mass during intense training could have been mediated by a calcium-induced reduction in PTH secretion. (Palmieri G M A. "Calcium: Why and how much?" Miner Electrolyte Metab 1995;21:236–241). However, it is also possible that other factors (e.g., these athletes might have increased their resistance weight training) could explain the increases in lean tissue observed. However, training changed little from the first year of training to the second and observations of players as well as interviews with players, coaches, trainers, and conditioning staff all indicated few, if any, changes in the training regimen.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of enhancing bone mineral content and enhancing lean tissue mass in a physically active subject wherein (i) the subject is in need of calcium due to a calcium deficit from physical activity, (ii) the physical activity is at an intensity of at least 60% of the maximum heart rate for the subject, and (iii) the total time of the physical activity per week is at least 80 minutes, comprising administering an effective amount of calcium to the subject, which is about 600 mg/day to 4000 mg/day for an effective period of time, thereby enhancing the bone mineral content and the lean tissue mass in the subject.

2. The method of claim 1, further comprising administering vitamin D to the subject.

3. The method of claim 1, wherein the source of the calcium comprises calcium-fortified orange juice.

4. The method of claim 1, wherein the physical activity is at an intensity of at least 70% of the maximum heart rate for the subject.

5. The method of claim 1, wherein the physical activity is at an intensity of at least 80% of the maximum heart rate for the subject.

6. The method of claim 1, wherein the physical activity is at an intensity of at least 85% of the maximum heart rate for the subject.

7. The method of claim 1, wherein the physical activity is at an intensity of at least 90% of the maximum heart rate for the subject.

8. The method of claim 1, wherein the total time of the physical activity per week is at least 160 minutes.

9. The method of claim 1, wherein the total time of the physical activity per week is at least 320 minutes.

10. The method of claim 1, wherein the effective amount of calcium is about 600 mg/day to 750 mg/day.

11. The method of claim 1, wherein the effective amount of calcium is about 600 mg/day to 1000 mg/day.

12. The method of claim 1, wherein the effective amount of calcium is about 600 mg/day to 2000 mg/day.

13. The method of claim 1, wherein the effective amount of calcium is about 600 mg/day to 3000 mg/day.

14. The method of claim 1, wherein the effective amount of calcium is about 600 mg/day to 3500 mg/day.

15. The method of claim 1, wherein the effective amount of calcium is about 750 mg/day to 4000 mg/day.

16. The method of claim 1, wherein the effective amount of calcium is about 1000 mg/day to 4000 mg/day.

17. The method of claim 1, wherein the effective amount of calcium is about 2000 mg/day to 4000 mg/day.

18. The method of claim 1, wherein the effective amount of calcium is about 800 mg/day to 3000 mg/day.

19. The method of claim 1, wherein the effective amount of calcium is about 1000 mg/day to 3000 mg/day.

* * * * *